United States Patent [19]

Kling et al.

[11] 4,412,832

[45] Nov. 1, 1983

[54] PEELABLE CATHETER INTRODUCTION DEVICE

[75] Inventors: John E. Kling; Larry R. Camin; Douglas W. Scott, all of Dallas, Tex.

[73] Assignee: Baxter Travenol Laboratories, Inc., Deerfield, Ill.

[21] Appl. No.: 259,281

[22] Filed: Apr. 30, 1981

[51] Int. Cl.³ .......................................... A61M 25/00
[52] U.S. Cl. ................................. 604/164; 604/161; 604/280
[58] Field of Search ............. 128/214.4, 221, 347–350, 128/DIG. 16; 604/161, 164–170, 280

[56] References Cited

U.S. PATENT DOCUMENTS

| 503,973 | 8/1893 | Lovejoy . | |
|---|---|---|---|
| 2,735,432 | 2/1956 | Hudson | 128/348 |
| 3,055,361 | 9/1962 | Ballard | 128/214 |
| 3,097,646 | 7/1963 | Scislowicz | 128/214 |
| 3,185,152 | 5/1965 | Ring | 128/214 |
| 3,219,036 | 11/1965 | Stafford | 128/214 |
| 3,359,978 | 12/1967 | Smith, Jr. | 128/214.4 |
| 3,382,872 | 5/1968 | Rubin | 128/214.4 |
| 3,500,828 | 3/1970 | Podhora | 128/214.4 |
| 3,515,137 | 6/1970 | Santomieri | 128/214.4 |
| 3,537,451 | 11/1970 | Beck | 128/214.4 |
| 3,550,591 | 12/1970 | MacGregor | 128/214.4 |
| 3,568,660 | 3/1971 | Crites et al. | 128/786 |
| 3,570,485 | 3/1971 | Reilly | 128/214.4 |
| 3,589,361 | 6/1971 | Loper et al. | 128/214.4 |
| 3,677,243 | 7/1972 | Nerz | 128/214.4 |
| 3,680,562 | 8/1972 | Wittes et al. | 128/347 |
| 3,730,187 | 5/1973 | Reynolds | 128/349 R |
| 3,821,957 | 7/1974 | Riely et al. | 128/348 |
| 3,860,006 | 1/1975 | Patel | 128/347 |
| 3,875,938 | 4/1975 | Mellor | 128/214.4 |
| 3,903,895 | 9/1975 | Alley et al. | 128/350 R |
| 3,921,631 | 11/1975 | Thompson | 128/214.4 |
| 3,938,530 | 2/1976 | Santomieri | 128/349 R |
| 4,016,879 | 4/1977 | Mellor | 128/214.4 |
| 4,020,835 | 5/1977 | Nordström et al. | 128/214.4 |
| 4,046,144 | 9/1977 | McFarlane | 128/214.4 |
| 4,068,659 | 1/1978 | Moorehead | 128/214.4 |
| 4,073,297 | 2/1978 | Kopp | 128/214.4 |
| 4,166,469 | 9/1979 | Littleford | 128/784 |
| 4,306,562 | 12/1981 | Osborne | 128/348 |
| 4,345,606 | 8/1982 | Littleford | 128/784 |

FOREIGN PATENT DOCUMENTS 21446 1/1981 European Pat. Off. .

OTHER PUBLICATIONS

"Desilets-Hoffman Peel Away Introducer Sets", Cook Incorporated Advertisement.

*Primary Examiner*—Dalton L. Truluck
*Attorney, Agent, or Firm*—Richards, Harris & Medlock

[57] ABSTRACT

An assembly (10) for the implantation of a peelable introductor catheter (24) through which a primary device (30) may be inserted having a slidable sleeve (18), which prevents premature disruption of the peelable catheter tube (12) and which also remains in position on the primary device after the introductor catheter tube has been peeled apart. The slidable sleeve (18) remains in place over the implanted primary device thereby serving to reinforce the primary device at the proximal end while at the same time providing a site at which the primary device may be secured to the patient (28).

8 Claims, 8 Drawing Figures

U.S. Patent  Nov. 1, 1983  4,412,832
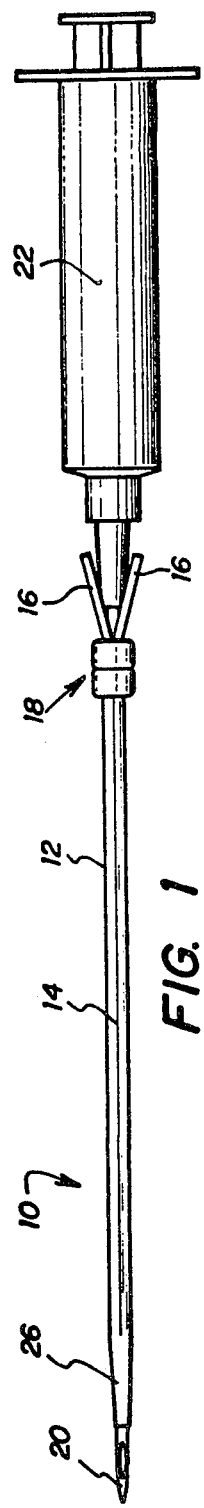
FIG. 1
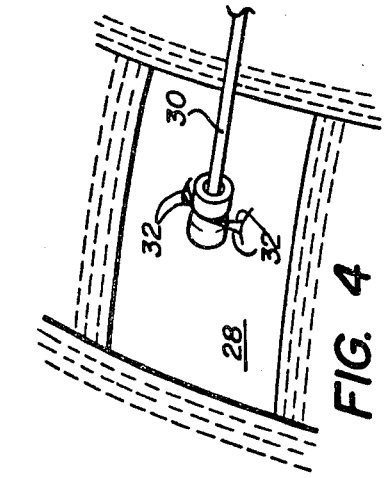
FIG. 4
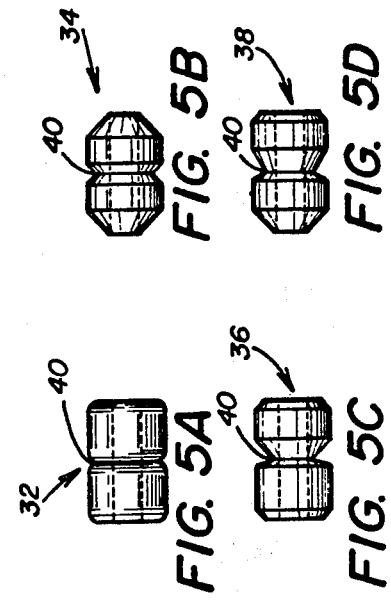
FIG. 5A  FIG. 5B
FIG. 5C  FIG. 5D
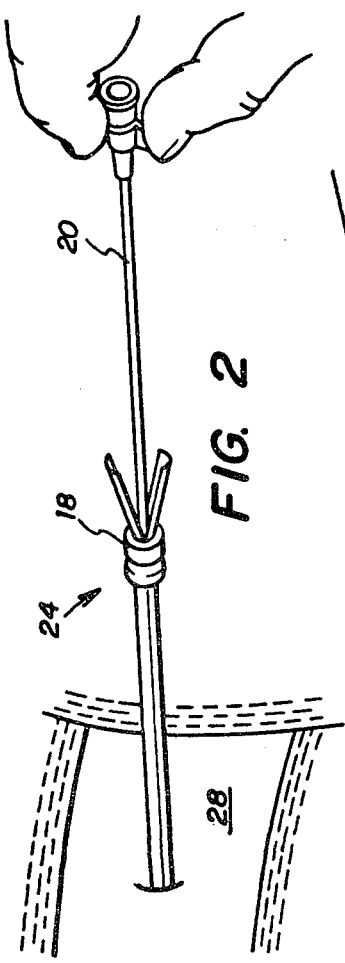
FIG. 2
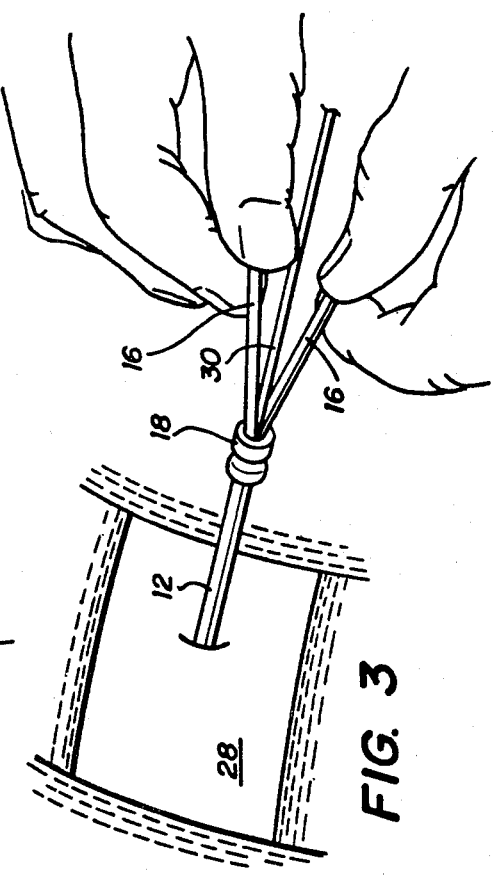
FIG. 3

PEELABLE CATHETER INTRODUCTION DEVICE

TECHNICAL FIELD

This invention relates to catheters and catheter introducer assemblies. More particularily, to a scored introducer catheter assembly for the implantation of a scored introducer catheter through which a primary device may be implanted within the patient, after which the introducer catheter may be removed from the patient and from the primary device leaving a sleeve for securing the primary device to the patient.

BACKGROUND ART

The use of cannulation in the medical arts is well known. Cannula may be used for many purposes, such as, taking of blood samples, transfusion of blood, infusion of medications, and introduction of diagnostic or therapeutic apparatus. Early cannula were generally of a rigid metal design, for example, the hypodermic needle. Repeated puncturing of veins within a short period of time with such rigid catheters tended to cause venous thromboses and subcutaneous hematomas. This frequently occured during normal hospitalization. To reduce injury and prevent soreness, the practice was developed of implanting a single rigid cannula into the lumen and performing successive procedures through the single catheter. When such a rigid needle (as used herein needle will mean a rigid hypodermic needle) was implanted within the patient, the risk existed that the needle would move relative to the lumen, puncturing the vein causing additional injury. In order to prevent movement of the needle relative to the body, it was necessary that the portion of the body where the needle was inserted to be immobilized. This resulted in considerable discomfort and potential injury to the patient.

Recognizing the discomfort and risk of injury associated with permitting a needle to remain in the body for an extended period of time, it was appreciated that replacing the needle with a flexible catheter was more desirable. This solution required that a method for implantation of such catheters be developed. Two systems were developed for inserting such flexible catheters. These methods are commonly referred to as "through-the-needle" and "over-the-needle".

The first method, "through-the-needle", utilized a hollow rigid catheter, needle, through which a flexible catheter could be inserted. Once the flexible catheter was in place the needle was removed from the body. The catheters implanted by this method were necessarily small. These small diameter piable catheters were difficult to manipulate because they were subject to bending, folding, and tearing. In addition, great care had to be exercised when retracting the needle from the patient and catheter, not to dislodge the catheter. Later needles were designed to minimize this risk. These needles could be opened along their logitudinal axis after being withdrawn from the patient, allowing the flexible catheter inside to be easily removed, as disclosed in U.S. Pat. No. 3,359,978 issued to Smith on Dec. 26, 1960 and entitled "Guide Needle for Flexible Catheters". A major disadvantage of this method was that the catheter to be inserted through the needle was relatively small and difficult to insert.

A second type of flexible catheter insertion is generally referred to as "over-the-needle". In this method, the flexible catheter is telescopically mounted over the rigid needle. The needle is inserted into the vein and the flexible catheter is then slid into the vein. Once the flexible catheter is placed the rigid needle is withdrawn from the lumen and the catheter. The major difficulty encountered with this system was that the flexible catheter had to be semi-rigid in order to penetrate the tissue. Although such catheters were semi-rigid, they were more preferable than a needle because they were relatively blunt ended and posed less of an injury risk than the needle.

To address the shortcomings of the through-the-needle and the over-the-needle concepts a third approach was developed which combined the two steps. The first step was to insert a semi-rigid introducer catheter by the over-the-needle technique. Once the needle was withdrawn from the semi-rigid introducer catheter a pliant infusion catheter was inserted through the introducer catheter. Once the infusion catheter was in place, the introducer catheter could be removed from the body and from around the infusion catheter. This method permits the use or a larger infusion catheter which is less vulnerable to tearing, buckling, bending or kinking. As a result, it may be more easily and quickly implanted thereby reducing the risk of injury during implantation. This method has also found use in the implantation of other devices, for example, pacemaker leads. As used herein "primary device" refers to the device which is inserted through the introducer catheter recognizing that it may be an infusion catheter, diagnostic or therapeutic device.

The present invention relates to an improved introducer catheter assembly design and the provision of a sleeve which functions to prevent premature splitting of the introducer catheter and, also, as a site for suturing the primary device to the patient. Those skilled in the art will appreciate that the introducer catheter of the present invention is not restricted to implantation by means of a needle only, but may also be implanted within the patient by making an incision in the patient.

DISCLOSURE OF THE INVENTION

In one aspect the present invention relates to an introducer catheter assembly for implantation of a scored introducer catheter tube to provide a path for introduction of a primary device, whereby the introducer catheter may be subsequently removed and discarded while the primary device remains in the operative position. In another aspect, the present invention relates to a slidable sleeve telescopically and slidably mounted over the introducer catheter tube about the proximal end to protect the scored catheter tube from accidential rupture, and which is slidably removed from the distal end of the introducer catheter tube end and onto the primary device to provide a suturing site.

In accordance with the present invention, an improved introducer catheter assembly is provided to be used in the implantation of a primary device. The introducer catheter tube is preferably constructed of semi-rigid materials and is beveled at the distal end. The catheter tube has been scored longitudinally in one or more places to provide lines along which the catheter tube may be split or peeled apart. The proximal end of the introducer catheter tube is preferably split to provide tabs by which the catheter may be grasp in order to facilitate removal from the tissue and splitting apart of the catheter tube, remove it from around the primary device.

A slidable sleeve is provided telescopically on the introducer catheter tube. Initially, the slidable sleeve is located on the proximal end of the introducer catheter tube at the termination of the split in the proximal end which defines the tabs. The slidable sleeve is made of an elastomeric material and is dimensioned to provide sufficient frictional force to prevent premature splitting of the proximal end of the introducer catheter upon introduction into the lumen. Once the needle is removed the sleeve continues to prevent the premature splitting of the introducer catheter tube while the primary device is being inserted through the introducer catheter. Once the primary device is implanted, the introducer catheter is removed from the tissue. The slidable sleeve is moved towards the distal end of the introducer catheter tube by the separation of the introducer catheter tube under the influence of manual force at the tabs. Once the introducer catheter tube has been completely pulled apart and removed from the primary device, the slidable sleeve remains telescopically disposed over the primary device and may be used to anchor the primary device to the patient by suturing the sleeve to the patient's skin.

BRIEF DESCRIPTION OF THE DRAWINGS

A more complete understanding of the invention and its advantages will be apparent from the Detailed Description taken in conjunction with the accompanying Drawings in which:

FIG. 1 is a side view of the introducer catheter assembly attached to a syringe;

FIG. 2 is a side elevational view of the introducer catheter implanted within a patient and a primary device (an infusion catheter) being inserted therethrough;

FIG. 3 is a side elevational view of the introducer catheter tube being removed from the patient and from about the primary device (infusion catheter) by manual disruption;

FIG. 4 is a top view of the primary device (infusion catheter) implanted within the patient with the slidable sleeve sutured to the patient; and FIGS. 5A, 5B, 5C and 5D are side views of various configurations of the slidable sleeve.

DETAILED DESCRIPTION

FIG. 1 illustrates the introducer catheter assembly indicated generally as 10, of the present invention. Introducer catheter assembly 10 includes a catheter tube 12 which is scored along one or more lines 14 to provide weakened areas along which introducer catheter tube 10 may be longitudinally split apart. The proximal end of the catheter tube 10 is split to provide tabs 16. Telescopically mounted over the catheter tube 12 is slidable sleeve 18 which is positioned on catheter tube 12 where the tabs 16 join to form the continuous cylindrical catheter tube 12. Slidable sleeve 18 and introducer catheter tube 12 are telescopically mounted over hypodermic needle 20, completing the assembly 10. The assembly 10 is attached to syringe 22.

The needle 20 allows blood to aspirate into the syringe 22 thus indicating to the technician or nurse that the needle 20 is properly placed in the vein. Once the needle 20 has been located in the lumen introducer catheter 24 (as used herein introducer catheter means the combination of the introducer catheter tube 12 and slidable sleeve 18) is positioned in the vein. The beveled distal end 26 of catheter tube 12 facilitates the insertion of a catheter through the skin and into the lumen. Once introducer catheter 24 is in position in the lumen, the needle 20 and syringe 22 are removed, thus, leaving the catheter 24 positioned in the body.

Although the introducer catheter is illustrated in conjunction with a needle for venipuncture, those skilled in the art will appreciate that the introducer catheter may be inserted without the use of a needle. For example, the introducer catheter may be positioned within the patient through a suitable incision.

FIG. 2 illustrates the introducer catheter 24 implanted in the patient 28 and a pliant infusion catheter 30 (the primary device) being inserted through the introducer catheter 24. Slidable sleeve 18 remains positioned at the proximal end of introductor catheter tube 12 where the split begins. In this position, sleeve 18 serves to reinforce the catheter tube 12, thus preventing premature disruption during insertion of the primary device illustrated here as infusion catheter 30. Once infusion catheter 30 is in position in the lumen, the introducer catheter tube 12 is grasped by the tabs 16 at the proximal end and then peeled apart and removed from the patient 28 as well as the infusion catheter 30, see FIG. 3. Infusion catheter 30 remains implanted in the operative position. As introducer catheter tube 12 is split apart slidable sleeve 18 is moved toward the distal end of the introducer catheter tube 12 and is slid onto infusion catheter 30, allowing the introducer catheter tube 12 to be completely pulled apart and removed from the patient and infusion catheter 30, see FIGS. 3 and 4.

FIG. 4 illustrates the infusion catheter 30 disposed within slidable sleeve 18 which is sutured to the patient 28 by sutures 32. In this position, slidable sleeve 18 provides protection for the proximal end of infusion catheter 30, a means to anchor the infusion catheter 30 to the patient 28, and reinforcement to the catheter 30 at its proximal end.

Introducer catheter tube 12 is preferably constructed from a semirigid plastic such as tetrafluoroethylene sold under the trademark "Teflon" by DuPont, or of any other polymer, for example polyvinyl chloride. A semirigid material is needed in order to give introducer catheter tube 12 sufficient strength to penetrate the tissue. If the primary device is an infusion catheter 30, it is preferably a soft pliant silicon rubber or like material which is compatible with the body. The slidable sleeve 18 is of any suitable elastomeric such as a silicon or polybutadiene copolymer.

FIGS. 5A, 5B, 5C and 5D show four embodiments of the slidable sleeve indicated as 32, 34, 36 and 38. The sleeve 18 is preferably molded with an area of reduced diameter 40 in which the sutures may rest and thus prevent movement of the sleeve. The sleeve may be beveled at one or both ends, for example sleeve 34, to eliminate edges which may cause discomfort to patients. Alternatively, the sleeve may be substantially cylindrical in form and made of material such that the sutures could be embedded within it. In general, the sleeve should be of sufficient length so that the frictional force resisting movement of the sleeve along the catheter tube is sufficient to prevent premature splitting of the catheter tube 12 during the prevent premature splitting of the tube during the implantation of the introducer catheter 24 and the primary device. The frictional force however should not be such as to prevent easy peeling apart of the catheter tube 12 by manual force applied by the fingers at tabs 16.

While one embodiment of the present invention has been described in detail herein and shown in the accompanying drawings, it will be evident that various further modifications are possible without departing from the scope of the invention.

We claim:

1. An introducer catheter through which an infusion catheter can be inserted into a lumen comprising:
   (a) an introducer catheter tube having a proximal end and a distal end;
   (b) said introducer catheter tube being provided with score lines along which said catheter may be split apart; and
   (c) a slidable sleeve telescopically disposed on the outer surface of said introducer catheter tube, said sleeve being slidable towards the distal end by force exerted upon it through said introducer catheter tube as it is disrupted.

2. The introducer catheter of claim 1 wherein said introducer catheter tube is beveled at the distal end such that the smallest outside diameter of said catheter tube is at the extreme distal end of said catheter tube.

3. The introducer catheter of claim 1 or 2 wherein said introducer catheter tube is partially split apart at the proximal end to provide tabs by which said introducer catheter tube may be grasped and peeled apart by manual manipulation thereby causing the slidable sleeve to move towards the distal end.

4. An introducer catheter assembly comprising:
   (a) a hollow needle having a distal end and a proximal end for venipuncture;
   (b) an introducer catheter tube having a proximal end and a distal end disposed telescopically over said needle and extending from the proximal end thereof;
   (c) said catheter tube being scored to provide weakened areas along which said introducer catheter may be split apart; and
   (d) a slidable sleeve telescopically disposed over said introducer catheter near a proximal end of said introducer catheter to prevent the premature splitting apart of the introducer catheter tube upon the insertion of the assembly, and further said sleeve being slidable towards the distal end of said introducer catheter by force exerted upon it through said introducer catheter tube as it is disrupted.

5. The assembly of claim 4 wherein said introducer catheter tube is partially split apart at the proximal end to provide tabs by which said introducer catheter may be grasped in order to be split apart.

6. The assembly of claim 5 wherein said slidable sleeve is positioned on said introducer catheter tube in the area where the split in the proximal end of the tube begins so as to prevent propagation of the split during insertion of any catheter assembly.

7. The assembly of claim 4 wherein said slidable sleeve is generally cylindrical with a reduced diameter section forming a channel suitable for engaging sutures.

8. In a two-step introduction assembly for introducing a scored introducer catheter into a lumen of a patient to provide a passageway for introduction of a primary device whereby the scored introducer catheter may be removed and discarded while the primary device remains in operative position, the assembly including a needle for venipuncture and scored introducer catheter tube having a proximal end and a distal end telescopically positioned over the needle having at least one longitudinal score line for substantially its entire length along which the catheter tube may be disrupted, the improvement comprising:

a slidable sleeve snugly engaging the introducer catheter tube and telescopically positioned about the proximal end of the catheter tube to protect the scored catheter tube from inadvertent separation along the score line, and being slidable distally under the influence of manual disruption of the scored catheter along the score line from the proximal end, whereby the scored catheter may be discarded after disruption along the score line while the sleeve remains in position on the primary device as a suturing site.

* * * * *